(12) United States Patent
Jadwizak et al.

(10) Patent No.: US 9,808,614 B2
(45) Date of Patent: Nov. 7, 2017

(54) IMPLANTABLE CURVED SHAPING PART FOR EXTERNALLY SHAPING AN IMPLANTABLE ELECTRODE LINE OR A CATHETER

(71) Applicant: BIOTRONIK SE & Co. KG, Berlin (DE)

(72) Inventors: Detmar Jadwizak, Erkner (DE); Carsten Fruendt, Berlin (DE); Dajana Kaiser, Berlin (DE); Gordon Hillebrand, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/078,288

(22) Filed: Mar. 23, 2016

(65) Prior Publication Data

US 2016/0303365 A1 Oct. 20, 2016

Related U.S. Application Data

(60) Provisional application No. 62/149,672, filed on Apr. 20, 2015.

(51) Int. Cl.
*A61N 1/375* (2006.01)
*A61N 1/05* (2006.01)
(Continued)

(52) U.S. Cl.
CPC ........... *A61N 1/05* (2013.01); *A61M 25/0054* (2013.01); *A61M 25/04* (2013.01); *A61N 1/057* (2013.01);
(Continued)

(58) Field of Classification Search
None
See application file for complete search history.

(56) References Cited

U.S. PATENT DOCUMENTS

| 5,925,073 A | 7/1999 | Chastain et al. |
| 6,103,037 A | 8/2000 | Wilson |
| (Continued) | | |

FOREIGN PATENT DOCUMENTS

| EP | 2 024 014 B1 | 11/2013 |
| WO | 2006116595 A1 | 11/2006 |

OTHER PUBLICATIONS

European Partial Search Report and Annex to the European Search Report on European Patent Application No. EP 16 16 1306, dated Sep. 26, 2016 (6 pages).

(Continued)

*Primary Examiner* — Brian T Gedeon
(74) *Attorney, Agent, or Firm* — Buchanan Ingersoll & Rooney PC

(57) ABSTRACT

An implantable curved shaping part for externally shaping an implantable electrode line or a catheter, wherein the shaping part has a continuous first lumen to allow a portion of the electrode line or of the catheter to pass through, wherein the shaping part has an extruded tube formed from two materials, each coextruded over a predetermined wall segment, having different shrinkage behavior or has a portion of an extruded spiral tube, wherein one of the coextruded materials or the material of the spiral tube has a high Shore hardness, in particular, of 60 Shore or more.

10 Claims, 5 Drawing Sheets

(51) Int. Cl.
*A61M 25/00* (2006.01)
*A61M 25/04* (2006.01)

(52) U.S. Cl.
CPC ............... *A61M 2025/006* (2013.01); *A61N 2001/0585* (2013.01)

(56) References Cited

U.S. PATENT DOCUMENTS

| | | | |
|---|---|---|---|
| 6,556,873 B1 | 4/2003 | Smits | |
| 8,086,317 B2* | 12/2011 | Finch | A61N 1/36017 |
| | | | 607/117 |
| 8,954,162 B2* | 2/2015 | Bonde | A61B 17/3468 |
| | | | 607/1 |
| 2003/0181966 A1 | 9/2003 | Morgan | |
| 2008/0147013 A1* | 6/2008 | Breton | A61M 25/0105 |
| | | | 604/174 |
| 2010/0114114 A1* | 5/2010 | Tockman | A61M 25/0147 |
| | | | 606/129 |
| 2010/0198208 A1* | 8/2010 | Napp | A61B 1/00078 |
| | | | 606/27 |
| 2016/0151608 A1* | 6/2016 | Aklog | A61M 25/04 |
| | | | 604/506 |

OTHER PUBLICATIONS

European Search Report and Annex to the European Search Report on European Patent Application No. EP 16 16 1306.2, dated Mar. 20, 2017 (9 pages).

\* cited by examiner

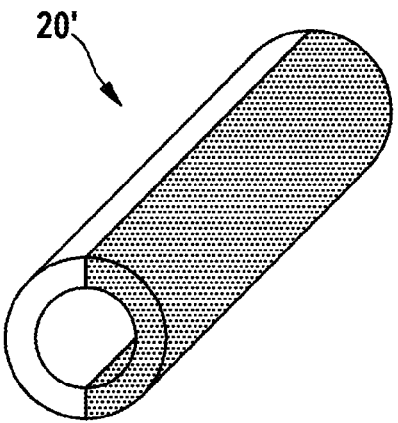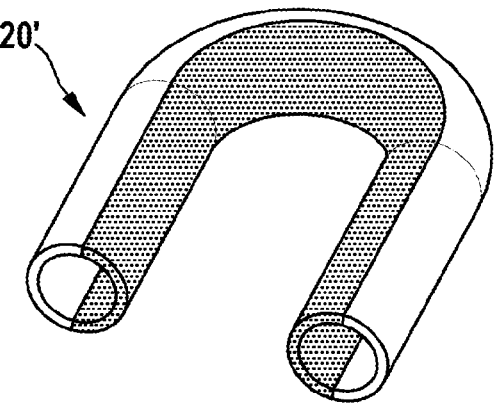
FIG. 2A    FIG. 2B
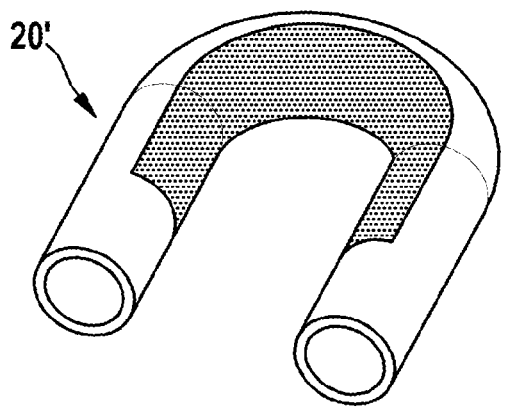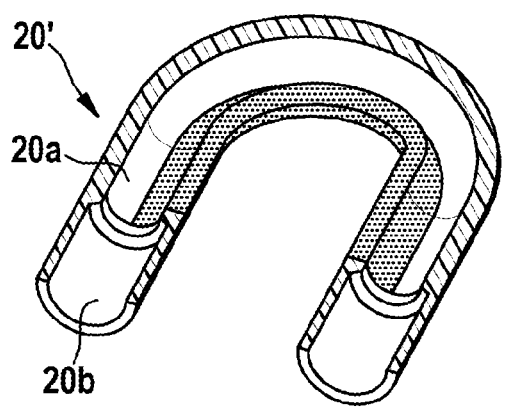
FIG. 2C    FIG. 2D

IMPLANTABLE CURVED SHAPING PART FOR EXTERNALLY SHAPING AN IMPLANTABLE ELECTRODE LINE OR A CATHETER

CROSS-REFERENCE TO RELATED APPLICATIONS

This patent application claims the benefit of U.S. Provisional Patent Application No. 62/149,672, filed on Apr. 20, 2015, which is hereby incorporated by reference in its entirety.

TECHNICAL FIELD

The present invention relates to an implantable curved shaping part for externally shaping an implantable electrode line or a catheter, wherein the shaping part has a continuous first lumen to allow a portion of the electrode line or of the catheter to pass through. The present invention also relates to an electrode line arrangement or catheter arrangement that is formed with at least one such shaping part.

BACKGROUND

Implanted medical electrode lines (also referred to as "electrodes" for short) have to be positioned in the body of the patient at a suitable point and also fixed sufficiently durably in this position in order to attain the desired therapeutic effects reliably and durably. A multitude of different developments for solving this problem have therefore been provided since the introduction of the first implantable cardiac pacemaker.

In order to fix electrode lines in vessel portions or relatively narrow hollow organs in a precisely positioned manner, electrode lines with impressed curvatures in the distal end region have already been proposed for some time, which, following the implantation and the removal of the guide wire or the stylet, tense up to a certain extent between opposite walls of the vessel or hollow organ on account of the curved profile of said electrode lines. A rather reliable position fixing that is also stable in the long term can thus be achieved. An example of such a construction is described in U.S. Pat. No. 5,925,073.

In this context, electrode lines having special inner structures have also been developed, with which a rigidity or flexibility that is variable over the longitudinal extent is to be provided; in this regard see U.S. Pat. No. 6,556,873 or European Patent No. 2 024 014 B 1, for example.

Special "CRT electrodes" are implanted in coronary sinus vessels in the region of the left ventricle. To this end, these electrodes have a "passive" fixing of the above-mentioned type, the distal region of the electrode being provided with one or more curvatures. During implantation, this curvature is put straight by an internally arranged stylet. If this stylet is withdrawn, the electrode returning into the curved state exerts force onto the vessel inner wall and, thus, anchors the electrode at the desired location thereof.

From a technical viewpoint the following possible implementations of such a solution are known and used:
1. Production of an electrode curvature by annealing an MP35N coil arranged in the line body.
2. Production of an electrode curvature by mechanical deformation (cold forming) of a coil arranged in the line body. This is preferably applied in the case of coradial coils, since here each individual wire has an insulation layer of which the melting point is below the annealing temperature of the coil and, therefore, an annealing process cannot be applied.
3. Production of an electrode curvature by thermal deformation of plastic insulation tubes.
4. Production of an electrode curvature by a silicone part injection molded in a curved mold.
5. Production of an electrode curvature by a silicone injection molded part with tension band.

All of these solutions have certain disadvantages, of which the following are specified here:

Firstly: With use of an ETFE-coated coradial coil, an annealing method cannot be applied. However, in order to form a plurality of poles in a small diameter, the use of such a coradial coil is necessary.

Secondly: The desired angle of curvature and the desired force of curvature are not produced by a mechanical deformation of the coil alone.

Thirdly: With use of silicone it is not possible to provide any subsequent thermal deformation. Silicone is an end-cross-linked material, which can no longer deform after the vulcanizing process. The use of silicone in the distal region of a CRT electrode is of great advantage, since flexibility and fatigue strength of a plastic material are superior for this application.

Fourthly: A silicone injection molded part that is injected in a curved shape does not produce the desired angle of curvature and the descried force of curvature (return force).

Fifthly: Due to the small diameter of an electrode line, only very small wall thicknesses are available for a tension band. Furthermore, a silicone injection molded part with tension band can be produced only in a complicated and complex production method with relatively high error potential.

The present invention is directed toward overcoming one or more of the above-mentioned problems.

SUMMARY

An object of the present invention is therefore to provide an improved solution for producing an electrode line (or also a catheter) that can be fixed passively in a vessel or relatively narrow hollow organ and that functions in particularly reliably and durably, can be easily handled during the implantation, and is also acceptable from cost aspects.

According to the fundamental considerations of the inventors, a silicone part is to be developed that, with a smaller diameter, low wall thickness, short length and simple production method, performs the function of curving a coradial coil and, thus, fixing the electrode in a vessel or hollow organ (especially in the coronary vessel). This silicone part must be flexible, be capable of being put straight, and must be durable and must also have the greatest possible return force.

At least the above object is achieved by an implantable curved shaping part having the features of Claim 1. Expedient developments of the inventive concept are specified in the dependent Claims. Furthermore, an electrode line arrangement having the features of Claim 6 and a catheter arrangement having the features of Claim 9 are provided.

The present invention includes the consideration of providing a separate shaping part for impressing a desired curvature onto an electrode line or a catheter tube, which shaping part essentially constitutes an extruded silicone tube or portion thereof in a technically simple and thus economical manner. So that such a silicone tube or silicone tube portion can perform the shaping function thereof, it must itself be bent or curved in the use state and must be able to generate a sufficiently high return moment in the event of a deformation (in the direction of a stretched state), such that the electrode line (or a catheter tube) to be shaped and received in the lumen of the shaping part does not prevent the return into the curved form but, rather, is "entrained" into the curved form during the return.

In accordance with a first aspect of the present invention, the shaping part has an extruded tube formed from two materials, each coextruded over a predetermined wall segment, having different shrinkage behavior, wherein one of the coextruded materials has a high Shore hardness, in particular of 60 Shore or more. The materials having different shrinkage behavior, in the event of the annealing step after the coextrusion, cause the tube to be curved in the finished state, and the incorporation of at least one material having a relatively high Shore hardness ensures a sufficiently high return moment in the above-mentioned sense.

In accordance with a relatively independent aspect of the present invention, the shaping part constitutes a portion of an extruded spiral tube made of a material having a high Shore hardness, again in particular of 60 Shore or more. The production of spiraled (helical) tubes by extrusion methods is an established technique and can also be applied with silicone tubes. In the context of the present invention, a sufficiently high rigidity or Shore hardness of the tube material must be ensured in order to attain a sufficiently large "force-intensifying" effect or return force. It goes without saying that this, for the specific implementation, must be coordinated with the properties of the electrode line or a catheter tube to be fixed. This is, of course, also true for the geometric dimensions (diameter and length) of the tube portion and expediently also for the helix diameter of the spiral tube used as a base.

In one embodiment of the present invention, the shaping part is formed as a part that is U-shaped or V-shaped in the use state with a rounded tip. The use state is understood to be the state with electrode line or catheter line or stiffening guide wire or stylet received in the shaping part. Depending on the length of the shaping part, the natural basic shape thereof (without electrode line or catheter line) may absolutely comprise a segment of a circle of more than 180°, and may even have in portions a coil or helix form.

In an embodiment that is preferred from this aspect, the shaping part has a silicone tube or silicone tube portion. In principle, however, the present invention is also possible with other suitable materials, in particular, with polymers that are licensed and approved for medical use.

In a further embodiment, the shaping part has ends that are overmolded with a material of arbitrary Shore hardness, for example, between 30 and 80 Shore. Lumen end portions are thus formed that have a widened diameter, such that space is created for an inner adhesive layer. These ends of the shaping part are preferably substantially stretched. For practical use of the electrode line or catheter arrangements in question, a fixed integral bond between the shaping part and a predetermined portion of the electrode line or catheter line (in particular, bordering an electrode pole) is to be created already from a licensing viewpoint. In order to achieve this without outer diameter enlargement (which would therefore be obstructive during use), space for a (in particular, annular) adhesive layer is to be created on the inner wall of the shaping part.

In an embodiment of the above-mentioned first aspect of the present invention, the coextruded materials of the extruded tube each occupy a semi-cylindrical wall segment. In principle, however, the two coextruded materials may also form different proportions of the wall of the shaping part, and the specific selection of the respective proportions may be dependent on the hardness of each of the respective material, the differences in shrinkage behavior and of course also the parameters of the electrode line or catheter tube to be shaped.

In accordance with one embodiment of the proposed electrode line arrangement, the shaping part completely surrounds a portion between two electrode poles, in such a way that a first end of the shaping part directly contacts a first electrode pole and a second end of the shaping part directly contacts a second electrode pole. The requirements mentioned further above with regard to the ongoing reliability, for example, in relation to insulation, tensile force and fatigue strength, which are also expressed in licensing requirements, are hereby taken into consideration.

In order to ensure a reliable connection between the shaping part and electrode poles, it is necessary to have inner heels at the ends of the shaping part for the required adhesive layer. The electrode poles also have a heel, such that sufficient adhesive area for reliable tensile force transmission, insulation and fatigue strength is provided. An end-face attachment alone, without stepped heels, might not satisfy these requirements.

In further embodiments of the electrode line arrangement, two or more U-shaped or V-shaped shaping parts are arranged in succession in the longitudinal direction on the electrode line with oppositely directed curvature, such that a distal end portion of the electrode line on the whole has impressed a substantially S-shaped, Z-shaped, J-shaped, undulating or zigzagged profile, in each case also 3-dimensionally.

Further embodiments, features, aspects, objects, advantages, and possible applications of the present invention could be learned from the following description, in combination with the Figures, and the appended claims.

DESCRIPTION OF THE DRAWINGS

Advantages and expedient features of the present invention will also emerge from the following description of exemplary embodiments with reference to the Figures, in which:

FIGS. 2A-2G show illustrations of a second exemplary embodiment of the present invention.

DETAILED DESCRIPTION

Figure 1A:
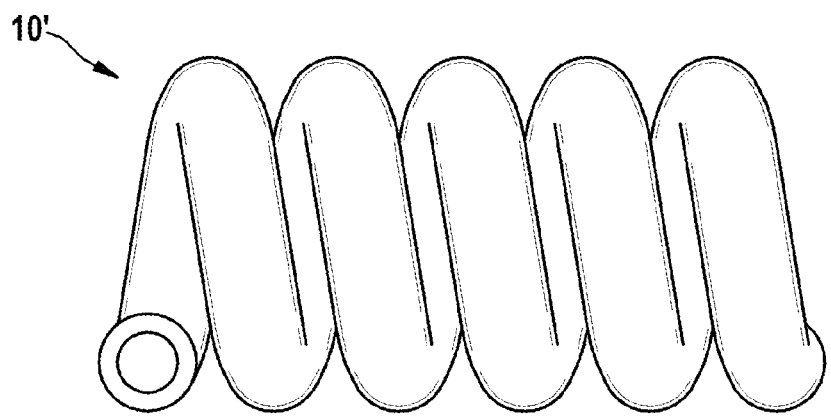
FIGS. 1A-1F show illustrations of a first exemplary embodiment of the present invention.
Figure 1B:
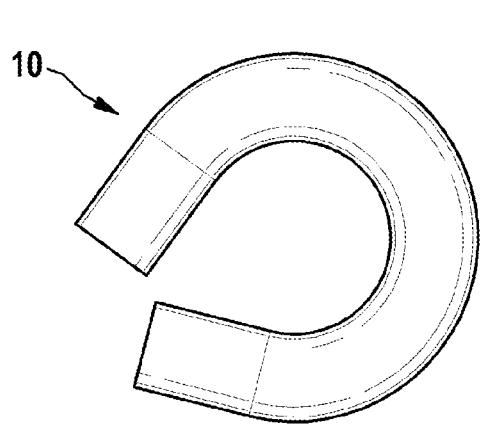
Figure 1C:
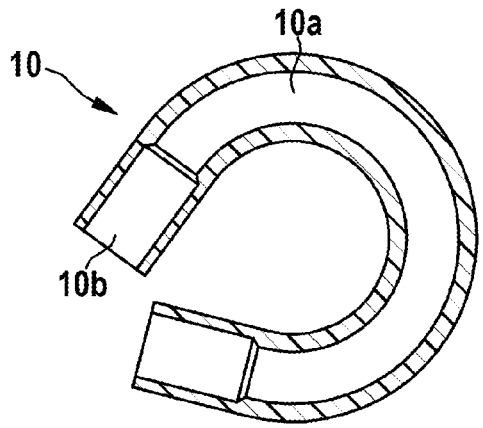

FIG. 1A shows a perspective illustration of a portion of an extruded silicone spiral tube 10' as preliminary product of the production of a shaping part according to the present invention; FIGS. 1B-1C show a shaping part 10 in a side view and longitudinal section, respectively; and FIGS. 1D-1F show differently shaped shaping parts 10A, 10B, 10C, respectively.

The spiral tube shown in FIG. 1A is produced by extrusion of a silicone tube stretched in a straight line with subsequent spiral shaping, or by extrusion of a spiral tube by means of a die mounted in a freely rotating manner in accordance with a method known per se. Here, a silicone material having a high Shore hardness, for example, 70 or 80 Shore, or any Shore in between, is used in order to utilize the high curving force that is associated with such a high rigidity or Shore hardness for a shaping part produced from the spiral tube.

The shaping part 10 illustrated in FIGS. 1B-1C is produced by trimming (cutting) a spiral tube portion of predetermined length from the spiral tube 10' according to FIG. 1A, and by subsequent injection of straight end portions in an injection mold. As can be seen in FIG. 1C, the end portions of the shaping part 10 are injected here with a diameter of their lumen 10b that is slightly enlarged compared with the inner diameter of the silicone tube portion (diameter of the lumen 10a). These end portions of enlarged diameter create space for an adhesive layer required during the subsequent assembly of the shaping part over an electrode line or a catheter tube. In order to produce the end portions, an injection molding compound having the Shore hardness to be set in accordance with the specific application is used, for example, a material having a Shore hardness between 30 and 80 Shore. Alternatively, an end portion of enlarged diameter can also be produced without injection molding process, more specifically, by milling the end portion contour of the spiral tube portion cut to size.

Figure 1D:
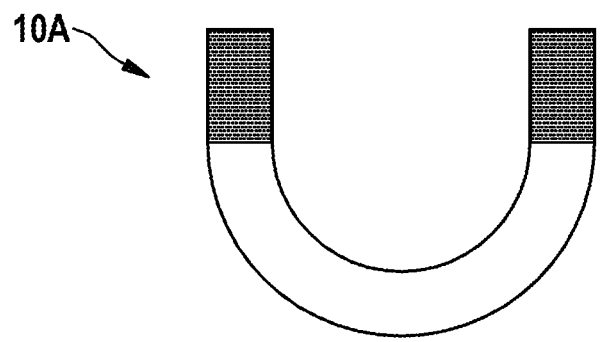
Figure 1E:
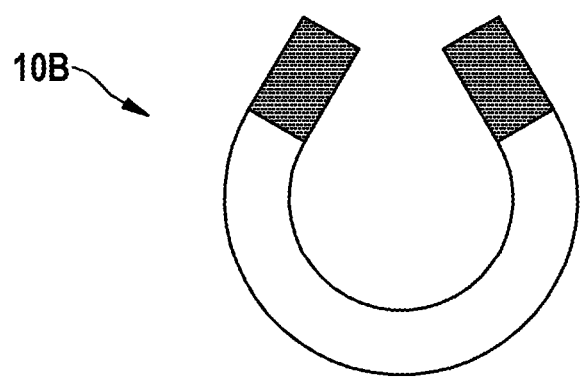
Figure 1F:
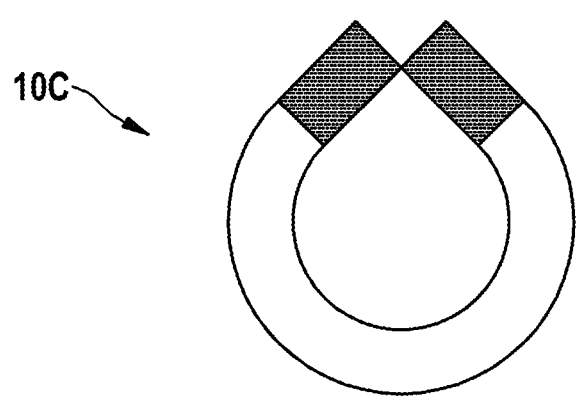

As is sketched in FIGS. 1C-1F, shaping parts with largely selectable form can be produced by use of a suitable preliminary product (spiral tube) with specially selected diameter and by selection of the length of the tube portion cut therefrom. In FIGS. 1D-1F, the end portions with widened inner diameter are in each case illustrated darker, but are not provided with separate reference signs. It goes without saying that, besides the variants sketched here, in which the portion of the shaping part in the form of the segment of a circle extends over an angular range between approximately 180° and approximately 270°, variants with smaller, but also larger angular extension of the portion in the form of a segment of a circle can also be provided. In addition, it should be mentioned that, with use of silicone having a high Shore hardness, the final angle of curvature or circle segment angle is greater, the smaller the diameter and the pitch of the spiral tube serving as preliminary product are selected to be.

Figure 2E:
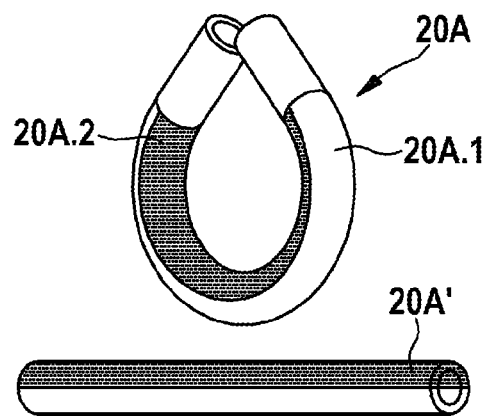
Figure 2F:
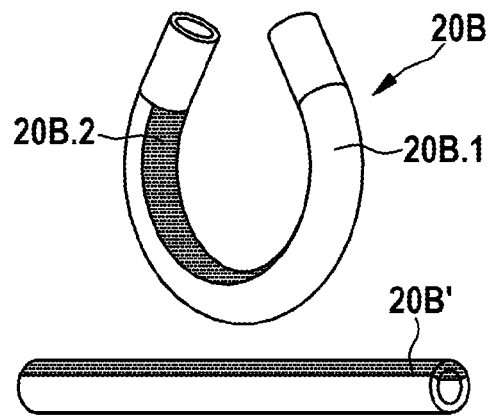
Figure 2G:
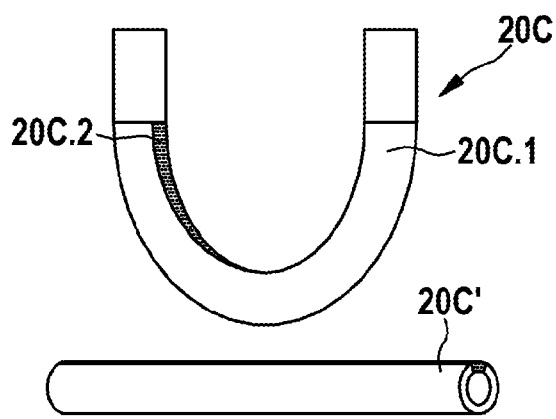

FIG. 2A schematically shows an elongate silicone tube portion and FIG. 2B shows the silicone tube portion in a state curved in a U-shape after an annealing step. FIGS. 2C-2D show a shaping part produced on this basis in a perspective illustration or perspective longitudinal sectional illustration; and FIGS. 2E-2G schematically show form variants of such a shaping part, in each case together with the tube portion stretched in a straight line serving as preliminary product. It should be noted that the preliminary product, and also the resultant shaping part, are formed from two different silicone materials having a different Shore hardness and resultant different shrinkage behavior, which is the reason for the formation of the curvature of the preliminary product and of the shaping part.

The U-shaped form shown in FIG. 2B of the silicone tube preliminary product 20' is thus produced by annealing, and different shrinkage behavior, provided here, of the primary silicone tube coextruded in a straight line from two silicone materials in accordance with a configuration as in FIGS. 2E-2G. An end portion having a lumen 20b that is widened compared with the lumen 20a of the primary tube is injected at both ends of the preliminary product curved in a U-shape. Similarly to the first embodiment described above, an annular gap for an adhesive reservoir is thus created.

FIGS. 2E-2G show different variants of the composition of the coextruded primary tube and different resultant forms of the shaping part produced on this basis. FIG. 2E shows a variant in which the two silicone materials 20.A1, 20.A2 in the preliminary product 20A' each occupy an angular range of 180° of the tube wall, thus giving a shaping part 20A of which the central portion in the form of the segment of a circle covers a circle segment angular range of approximately 270°. According to FIG. 2F a silicone material 20.B2 has a proportion of significantly less than 180° of the wall of the preliminary product 20b', and after the annealing and the injection of the end portions, a shaping part 20B is provided of which the central portion shaped in the form of a segment of a circle extends over an angular range of approximately 220°. FIG. 2G lastly shows a stretched tube portion 20C', in which the two silicone materials 20.C1, 20.C2 have a very significantly different proportion in the tube wall, thus resulting ultimately (after annealing and injection of end portions) in a shaping part having an approximate U-shape, i.e., an angular extension of the portion shaped in the form of a segment of a circle of approximately 180°.

Of course, besides the suitable selection of the proportion of the two material components during coextrusion of the tube portion serving as preliminary product, the difference in the Shore hardness and in the shrinkage behavior is also important for the formation of a desired end form of the shaping part. The corresponding material sizes and forms, produced after the annealing, of conventional medical silicones are known to a person skilled in the art, such that these do not have to be specified in greater detail at this juncture.

Figure 3A:
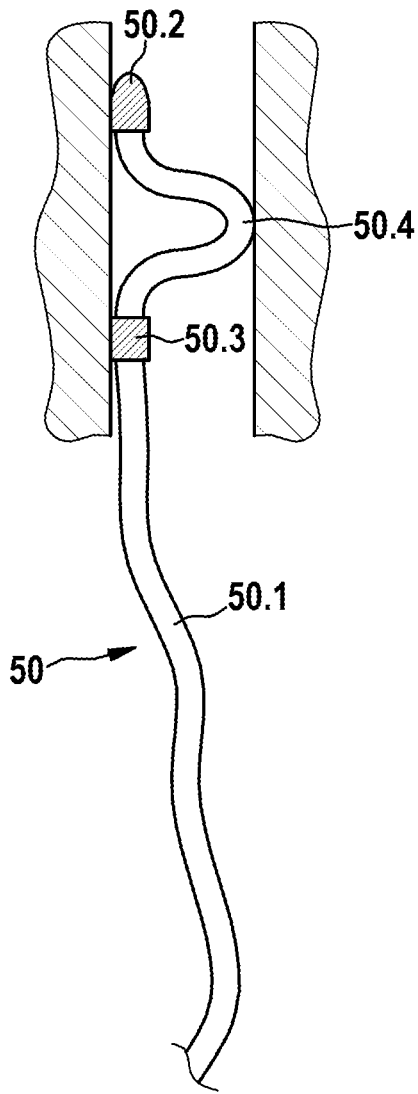
FIGS. 3A-3B show perspective illustrations of two embodiments of an electrode line arrangement according to the present invention.
Figure 3B:
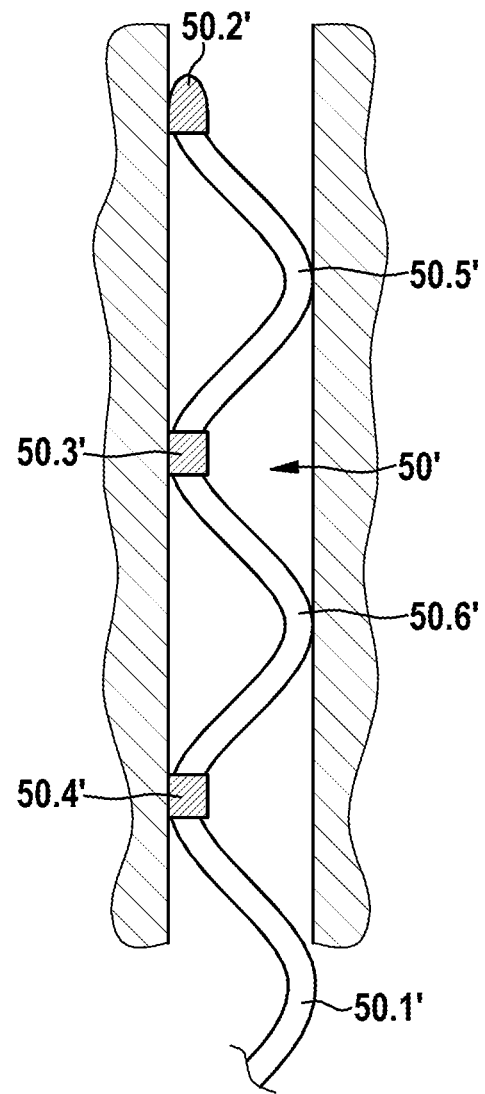

FIGS. 3A-3B show two configurations of electrode line arrangements that can be provided with shaping parts of the above-described type. FIG. 3A shows an electrode line arrangement 50 with an electrode line (electrode) 50.1, which has a tip electrode 50.2 and a ring electrode 50.3 as electrode poles and is deformed so as to be V-shaped in the end portion by a shaping part 50.4 shrunk-fit on the line between the two electrode poles 50.2, 50.3. The electrode line arrangement 50 thus tenses between the opposite walls of a vessel which, in turn, leads in a desirable manner due to the fact that the electrode poles 50.2 and 50.3 have reliable wall contact and can thus reliably performed their stimulation and/or sensing task in a durable manner.

FIG. 3B shows, as a modification of this configuration, a further electrode line arrangement 50', which comprises a three-pole electrode line 50.1' with the electrode poles 50.2', 50.3' and 50.4' and two shaping parts 50.5', 50.6'. Both shaping parts are each placed between the three electrode poles around the corresponding portions of the electrode 50.1', and are tightly glued there to the electrode. It can be seen that the electrode line in this embodiment has assumed a form that is undulating on the whole in the end portion, wherein this form in turn has the desired result that all electrode poles 50.2', 50.3' and 50.4' have reliable wall contact.

In addition, the present invention can also be embodied in a multitude of modifications of the examples shown here and aspects of the invention highlighted above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable curved shaping part for externally shaping an implantable electrode line or a catheter, wherein the shaping part has a continuous first lumen to allow a portion of the electrode line or of the catheter to pass through, wherein the shaping part has an extruded tube formed from two materials, each coextruded over a predetermined wall segment, having different shrinkage behavior or has a portion of an extruded spiral tube, wherein one of the coextruded materials or the material of the spiral tube has a high Shore hardness of 60Shore or more.

2. The shaping part according to claim 1, formed as a part that is U shaped or V shaped in the use state with rounded tip.

3. The shaping part according to claim 1, which has a silicone tube or silicone tube portion.

4. The shaping part according to claim 1, having ends that are overmolded with a material of lower Shore hardness of 40 Shore or less, whereby lumen end portions are formed that have a widened diameter, such that space for an inner adhesive layer is created.

5. The shaping part according to claim 1, wherein the coextruded materials of the extruded tube each occupy a semi-cylindrical wall segment.

6. An electrode line arrangement having an implantable electrode line and at least one shaping part according to claim 1, which surrounds a distal portion of the electrode line.

7. The electrode line arrangement according to claim 6, wherein the shaping part completely surrounds a portion between two electrode poles in such a way that a first end of the shaping part directly contacts a first electrode pole and a second end of the shaping part directly contacts a second electrode pole.

8. The electrode line arrangement according to claim 6, wherein two or more U shaped or V shaped shaping parts are arranged in succession in the longitudinal direction on the electrode line optionally with oppositely directed curvature, such that a distal end portion of the electrode line on the whole has a substantially S-shaped, Z-shaped, J-shaped, undulating or zigzagged profile.

9. A catheter arrangement having a catheter and at least one shaping part according to claim 1.

10. The shaping part according to claim 1, wherein the two different coextruded materials of the extruded tube each occupy an angular portion of a cylindrical wall segment, and wherein different angular extents of the two different materials about the cylindrical wall results in different resultant forms of the shaping part after annealing.

* * * * *